(12) United States Patent
Chin

(10) Patent No.: US 9,402,531 B2
(45) Date of Patent: Aug. 2, 2016

(54) ENDOSCOPIC CANNULAS AND METHODS OF USING THE SAME

(71) Applicant: Pavilion Medical Innovations, LLC, Norwell, MA (US)

(72) Inventor: Albert K. Chin, Palo Alto, CA (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 338 days.

(21) Appl. No.: 13/791,107

(22) Filed: Mar. 8, 2013

(65) Prior Publication Data

US 2014/0012083 A1      Jan. 9, 2014

Related U.S. Application Data

(60) Provisional application No. 61/668,173, filed on Jul. 5, 2012, provisional application No. 61/670,319, filed on Jul. 11, 2012.

(51) Int. Cl.

| | |
|---|---|
| *A61B 1/00* | (2006.01) |
| *A61B 1/04* | (2006.01) |
| *A61B 1/06* | (2006.01) |
| *A61B 17/00* | (2006.01) |
| *A61B 17/34* | (2006.01) |
| *A61M 1/00* | (2006.01) |
| *A61M 25/01* | (2006.01) |
| *A61B 1/015* | (2006.01) |
| *A61B 1/018* | (2006.01) |
| *A61B 17/30* | (2006.01) |

(52) U.S. Cl.
CPC .............. *A61B 1/00154* (2013.01); *A61B 1/015* (2013.01); *A61B 1/018* (2013.01); *A61B 17/3421* (2013.01); *A61B 17/3478* (2013.01); *A61M 1/00* (2013.01); *A61M 25/01* (2013.01); *A61B 2017/00247* (2013.01); *A61B 2017/00907* (2013.01); *A61B 2017/308* (2013.01); *A61B 2017/3454* (2013.01)

(58) Field of Classification Search
CPC ............. A61B 1/0008; A61B 1/00094; A61B 1/00131; A61B 1/00133; A61B 1/00147
USPC ......... 600/104, 109, 112–114, 127, 156, 172, 600/183, 106, 107, 115, 129, 158, 159, 175, 600/374; 606/129, 190

See application file for complete search history.

(56) References Cited

U.S. PATENT DOCUMENTS

| | | | |
|---|---|---|---|
| 7,526,342 B2 | 4/2009 | Chin et al. | |
| 2003/0187460 A1* | 10/2003 | Chin et al. | 606/129 |
| 2003/0187461 A1* | 10/2003 | Chin | 606/129 |

(Continued)

*Primary Examiner* — Ryan Henderson
(74) *Attorney, Agent, or Firm* — Greenberg Traurig, LLP; Chinh H. Pham; Roman Fayerberg (57) ABSTRACT

Endoscopic cannulas and methods of their use are disclosed. In some embodiments, an endoscopic cannula may include an elongated body having a proximal end and a distal end. A viewing channel and a working channel may extend through the elongated body. The viewing channel can be configured for passing therethrough an endoscope to the distal end of the elongated body for viewing outside the elongated body, while the working channel can be configured for passing therethrough an injection needle distally of the elongated body. The cannula may also include a suction pod disposed on a bottom surface of the elongated member, the suction pod being in communication with a suction channel extending through the elongated body to create suction between the suction pod and a tissue surface to temporary attach the elongated body to the tissue surface.

10 Claims, 8 Drawing Sheets

(56) References Cited

U.S. PATENT DOCUMENTS

| | | | |
|---|---|---|---|
| 2003/0212446 A1* | 11/2003 | Kaplan et al. | 607/129 |
| 2004/0153098 A1 | 8/2004 | Chin et al. | |
| 2004/0216748 A1 | 11/2004 | Chin et al. | |
| 2006/0100480 A1* | 5/2006 | Ewers et al. | 600/114 |
| 2008/0214895 A1* | 9/2008 | Campos | 600/129 |
| 2008/0262300 A1* | 10/2008 | Ewers et al. | 600/114 |
| 2009/0023983 A1* | 1/2009 | Stefanchik | 600/104 |
| 2009/0048486 A1* | 2/2009 | Surti | 600/127 |
| 2009/0131907 A1 | 5/2009 | Chin et al. | |
| 2010/0240952 A1* | 9/2010 | Okazaki et al. | 600/109 |

* cited by examiner

ENDOSCOPIC CANNULAS AND METHODS OF USING THE SAME

RELATED APPLICATIONS

This application claims the benefit of and priority to U.S. Provisional Application No. 61/668,173, filed on Jul. 5, 2012, and U.S. Provisional Application No. 61/670,319, filed on Jul. 11, 2012, and the entireties of both of these applications are incorporated herein by reference.

TECHNICAL FIELD

The presently disclosed embodiments relate to endoscopic cannulas and methods of their use.

BACKGROUND

Procedures for injecting substances into organs has traditionally been cumbersome and difficult. Such procedures cannot be easily affectuated through a minimally invasive approach. For example, ability to regenerate adult heart tissue is a promising approach to treating cardiac disease. Injection of cells or factors affecting endogenous cells into the beating heart in the endoscopic procedure must be performed carefully to avoid complications. If a needle is used to inject the substances, the needle must be properly oriented and under sufficient control to ensure that the needle does not puncture a coronary vein or artery and cause hemorrhage within the pericardial space, with subsequent cardiac tamponade. Movement of the beating heart further complicates needle placement because of erratic movement of the coronary vessels as needle insertion is attempted. Prior art methods require multiple users to perform the injection.

SUMMARY OF THE INVENTION

Endoscopic cannulas and methods of their use are disclosed. In some embodiments, an endoscopic cannula may include an elongated body having a proximal end and a distal end. A viewing channel and a working channel may extend through the elongated body. The viewing channel can be configured for passing therethrough an endoscope to the distal end of the elongated body for viewing outside the elongated body, while the working channel can be configured for passing therethrough an injection needle distally of the elongated body. The cannula may also include a suction pod disposed on a bottom surface of the elongated member, the suction pod being in communication with a suction channel extending through the elongated body to create suction between the suction pod and a tissue surface to temporary attach the elongated body to the tissue surface.

In some embodiments, an endoscopic cannula may include an elongated body having a superior aspect and an inferior aspect. A viewing channel may extend through the elongated member through which channel an endoscope can be passed to the distal end of the elongated body for viewing outside the elongated body. A working channel may also extend through the elongated body of the cannula. The working channel may allow an injection needle to be passed through the working channel distally of the elongated body. The cannula also includes a suction pod disposed on a bottom surface of the inferior aspect of the elongated member, the suction pod being in communication with a suction channel extending through the elongated body to create suction between the suction pod and a tissue surface to temporary attach the elongated body to the tissue surface.

In some embodiments, a method of injecting a substance into a heart of a patient is provided, the method includes disposing an endoscope in a viewing channel extending through an elongated body for viewing outside the elongated body. Then the elongated body may be advanced, under endoscopic visualization, into a intra-pericardial space anterior to the surface of the heart. Negative pressure may be applied to a suction channel extending through the elongated body to create a suction force between a suction pod disposed on a bottom surface of the elongated member and an epicardial surface to attach the elongated body to the epicardial surface. Then, an injection needle can be passed through a working channel extending through the elongated body distally of the elongated body to inject a substance into the heart.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The cannulas of the present disclosure enable a single user to visualize and navigate around the surface of a tissue or organ to be injected, stabilize a portion of the tissue or organ near the injection site, and inject substances into the tissue or organ under direct visual control. The cannulas of the present disclosure may include means for orienting an injection needle and aligning the needle with the injection site. In some embodiments, the endoscopic cannulas of the present disclosure are used to inject substances into the heart. In such embodiments, the cannulas of the present disclosure enable a single user to visualize and navigate around the tissue surface of the heart, stabilize a portion of the beating heart, and precisely inject substances into the myocardium under direct visual control.

In some embodiments, an endoscopic cannula of the present disclosure may include an elongated body having a proximal end and a distal end. The cannula may also include a viewing channel for passing an endoscope to the distal tip of the elongated body for viewing outside the elongated body. A working channel for passing an injection needle distally of the elongated body may also be included. The endoscopic cannula of the present disclosure may further include a suction pod disposed on an attachment surface of the elongated member. This suction pod, in one embodiment, may be in communication with a suction channel extending through the elongated body to create suction between the suction pod and a tissue surface to temporary secure the elongated body to the tissue surface.

In some embodiments, a method of injecting a substance into the heart of a patient includes disposing an endoscope in a viewing channel that extends through an elongated body for viewing outside the elongated body. Next, the elongated body may be advanced, under endoscopic visualization, into an intra-pericardial space anterior to the surface of the heart. Subsequently, a negative pressure may be applied to a suction channel extending through the elongated body to create a suction force between a suction pod disposed on an outer surface of the elongated member and an epicardial surface to secure the elongated body to the epicardial surface. Once the elongated body is secured to the epicardial surface, an injection needle may be passed through a working channel that extends through the elongated body distally of the elongated body to inject a substance into the heart.

Figure 1:
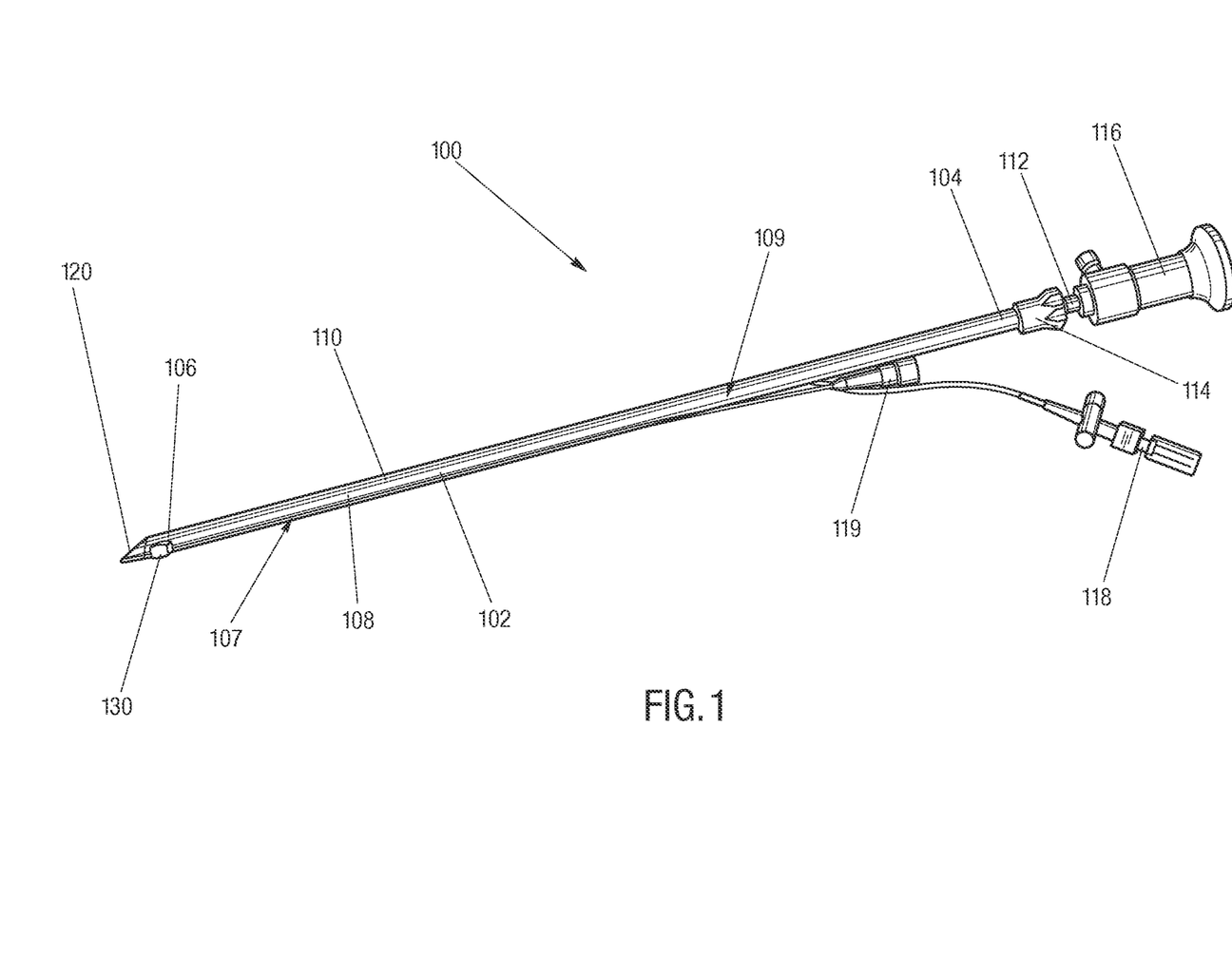
FIG. 1 illustrates a perspective view of an endoscopic cannula of the present disclosure.

Referring to FIG. 1, an endoscopic cannula 100 of the present disclosure includes an elongated body 102 having a proximal end 104 and a distal end 106. In some embodiments, the elongated body 102 may be configured for passing extravascularly through an entry incision to a site of injection on a surface of a tissue or an organ. The elongated body 102, in some embodiments, may be made of a biocompatible material, such as metal, plastic or another material. To aid in navigating the elongated body 102 to a site of injection, the elongated body 102 may be sufficiently rigid axially along its length. To provide the elongated body 102 with such characteristic, in an embodiment, the elongated body 102 may be made from a plastic material, metallic material, shape memory material, composite material or any other materials that has the desired characteristics. To the extent desired, the elongated body 102 may be provided with some flexibility to move radially from side to side depending on the application.

From the perspective shown in FIG. 1, the elongated body 102, in some embodiments, can include an inferior aspect 107 having a bottom surface 108 that may be adapted for placement on a tissue surface, as is described below, and a superior aspect 109 with a top surface 110 opposite the bottom surface 108. In some embodiments, the elongated body 102 may be provided with a suction pod 130 on the bottom surface 108 for securing or attaching the elongated body 102 to tissue surface. In some embodiments, the bottom surface 108 may include a feature to provide a landmark for orientating the endoscopic cannula 100 on the tissue surface to align it with the injection site. In some embodiments, the bottom surface 108 may be substantially flat or even so as to facilitate orientating the endoscopic cannula 100 on the tissue surface. In some embodiments, providing the elongated body 102 with a flat bottom surface 108 may also facilitate stabilization of the endoscopic cannula 100 on the tissue surface.

The endoscopic cannula 100 may include a viewing port 112 with an adapter 114 at the proximal end 104 for advancing an endoscope 116 into the endoscopic cannula 100. In addition to the viewing port 112, the endoscopic cannula 100 may also include one or more adapters 118, 119, in communication with additional one or more inner lumens of the endoscopic cannula 100, as is described in more detail below.

Figure 2:
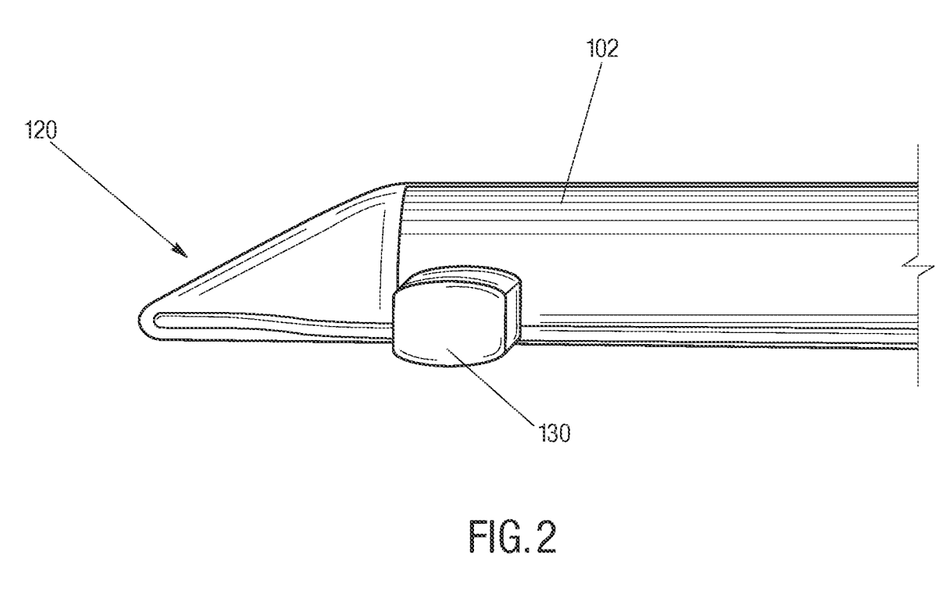
FIG. 2 is a close-up view of the distal tip of an endoscopic cannula of the present disclosure.

In reference to FIG. 2, in some embodiments, the endoscopic cannula 100 may include a visualization tip 120 disposed at or about the distal end 106 of the endoscopic cannula 100. The tip 120 may be transparent to allow for endoscopic viewing through the tip 120. The visualization tip 120 may be provided with any shape, as long as it facilitates endoscopic viewing therethrough. In some embodiments, the tip 120 may be blunt or rounded to avoid injuring surrounding tissues as the endoscopic cannula 100 is navigated to a site of injection. In some embodiments, to aid in tissue dissection, the tip 120 may be substantially sharp or sloping.

Figure 3A:
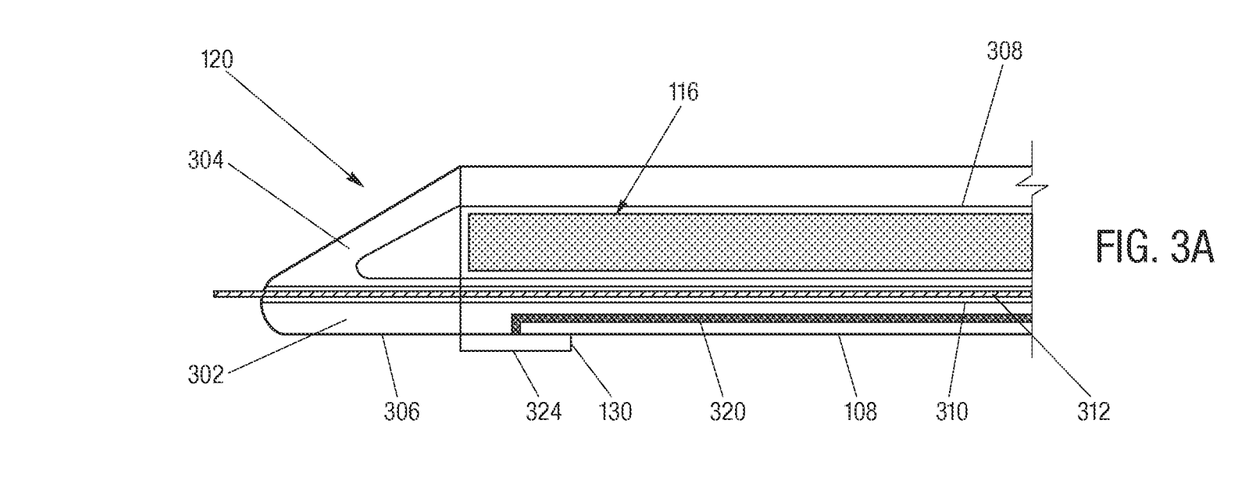
FIG. 3A and FIG. 3B are a side view and a bottom view, respectively, of an endoscopic cannula of the present disclosure.

In reference to FIG. 3A, in some embodiments, the visualization tip 120 may be beveled with a substantially straight lower region 302, and a tapered upper region 304. In operation, the straight lower region 302 may be positioned on the surface of the tissue to which the endoscopic cannula 100 is attached. As is disclosed in detail below, a working channel for advancing a needle may be extended through the straight lower region 302 of the visualization tip 120. Providing the visualization tip 120 with the straight lower region 302 may help to minimize possible disturbances created by the working channel to the endoscopic visual field. In this manner, the working channel extending to the distal tip of the visualization tip 120 through the straight lower region 302 of the visualization tip 120 may avoid cutting across the path of the endoscope lens, which may obscure a major portion of the visual field, and render the injection difficult and dangerous. In some embodiments, an outer surface 306 of the bottom straight lower region 302 may be aligned with the bottom surface 108 of the elongated body 102 of the endoscopic cannula 100 to form a continuous bottom surface of the endoscopic cannula 100. In some embodiments, the outer surface 306 of the straight lower region 302 may be flat or even, similar to the bottom surface of the elongated body 102.

In reference to FIG. 3A, in combination with FIG. 1, the endoscopic cannula 100 includes a viewing channel 308 extending between the viewing port 112 and visualization tip 120. The viewing channel 308 may be sized to accommodate an endoscope 116 to allow the endoscope to be advanced from the viewing port 112 into the visualization tip 120. In some embodiments, the viewing channel 308 may extend substantially through the superior aspect 109 of the elongated body into the tapered upper region 304 of the visualization tip 120. In some embodiments, the viewing channel 308 may terminate at its distal end in a bevel, imitating the shape of the visualization tip 120.

In continued reference to FIG. 3A, the endoscopic cannula 100 may also include an open working channel 310 in fluid communication with the adapter 119 and through the visualization tip 120 to allow passing of surgical instruments or materials to the site of injection. In some embodiments, the working channel 310 may be sized to accommodate slidable movement therein of a hollow injection needle 312, which can be used to inject one or more substances into tissue or organ. The working channel 310 may be positioned between the viewing channel 308 and the bottom surface 108 of the elongated body 102. In some embodiments, the working channel 310 may be positioned substantially in the inferior aspect 107 of the elongated body 102 of the endoscopic cannula 100 and straight lower region 302 of the visualization tip 120. In some embodiments, the working channel 310 may pass through the apex of the visualization tip 120. Position of the working channel 310 with respect to the viewing channel 308 may be selected to optimize viewing with of the endoscope 116 situated in the visualization tip 120 of an injection into the tissue or organ with the injection needle 312. For example, the working channel 310 may be placed in relation to the viewing channel 308 such that the injection needle 312 may be observed as it exits from the working channel 310 and remains visible as the injection needle 312 is advanced to and inserted into the myocardium. In some embodiments, the working channel 310 may be positioned to minimize disturbances to the endoscopic visual field.

Still referring to FIG. 3A, the endoscopic cannula 100 may also include a suction pod 130 disposed on the bottom surface 108 of the elongated member 102. The suction pod 130 may be in fluid communication with the adapter 118, such as a vacuum control valve, by a suction channel 320. The suction pod 130 may be designed to facilitate temporary stabilization of the endoscopic cannula 100 on the tissue surface when a negative pressure is applied to the suction pod 130. In some embodiment, the suction pod 130 may be made from a porous material or include suction ports extending between the inner surface and the outer surface of the suction pod 130. In this manner, the tissue surface may adhere to the endoscopic cannula 100 by creating a suction force between the tissue surface and the endoscopic cannula 100. In some embodiments, the suction force may be normal to the tissue surface. To the extent desired, an irrigation fluid may be injected into the suction pod 130 after the suction is turned off to detach the endoscopic cannula 100 from the tissue surface.

In some embodiment, the suction pod 130 may have a bottom surface 324 that is provided with a shape similar to the shape of the bottom surface of the elongated body 102. In some embodiment, the bottom surface 324 of the suction pod 130 may be flat and may be substantially parallel to the flat bottom surface of the elongated body 102.

The suction pod 130 may be located at or near the distal end 106 of the elongated body 102. In some embodiments, the suction pod 130 may be located sufficiently close to the distal end 106 of the elongated body to enable stabilization of the tissue in proximity to the needle injection site, maximizing injection precision and control during needle advancement and injection, despite potential tissue movement.

Figure 3B:
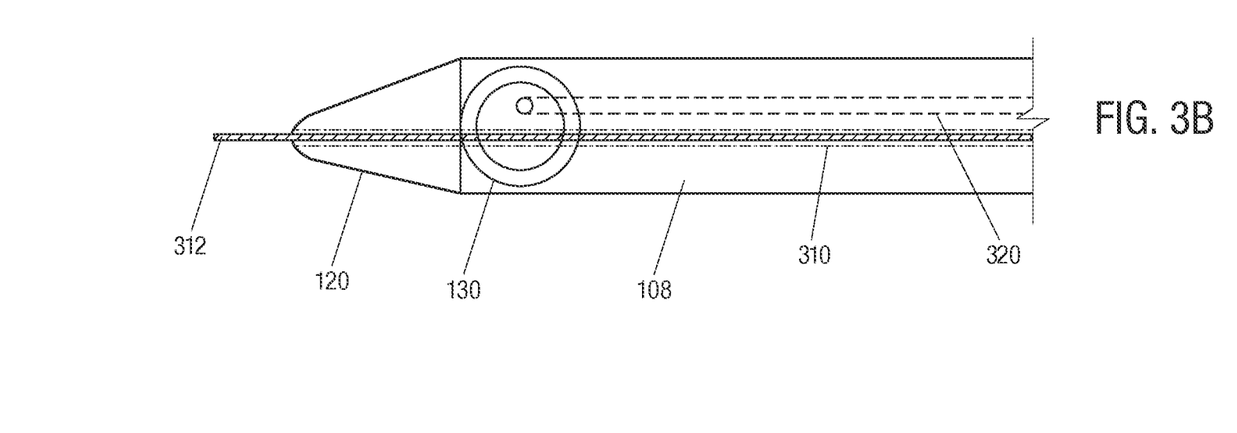

In reference to FIG. 3B, in some embodiments, the working channel 310 may be centered in the inferior aspect of the cannula and the conical tip. On the other hand, in some embodiments, the suction channel 320 may be offset to one side of the working channel 310.

Figure 4:
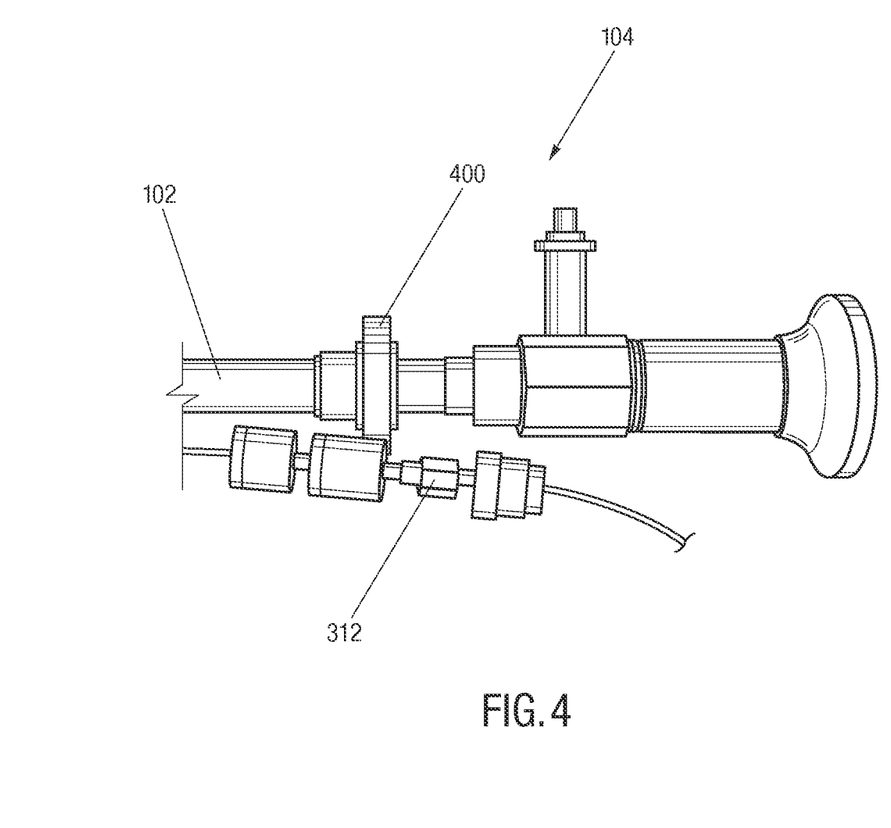
FIG. 4 illustrates a close-up view of the proximal end of an endoscopic cannula of the present disclosure.

In reference to FIG. 4, the endoscopic cannula 100 may further include an actuator 400 to support an injection needle 312 and to prevent kinking of the injection needle during use. Typically, a small-diameter injection needle may be advanced through a channel in the endoscopic cannula and the inferior aspect of the visualization tip. The needle can be used to inject therapeutic agents into the myocardium. The hub of the needle may typically extend out of the proximal end of the endoscopic cannula to attach to a syringe with the substance to be injected. The length and small diameter of the injection needle may make lead to kinking of the injection needle, particularly with the weight of the attached syringe, therefore rendering the injection needle inoperable. In some embodiments, the actuator 400 may be a collar that can slide along the proximal end of the elongated body 102 of the endoscopic cannula 100. The actuator 400 may attach to the injecting injection needle 312 near its hub. In this manner, advancing the actuator 400 can advance the injecting injection needle 312 from the distal end of the endoscopic cannula 100. When the sliding actuator 400 is advanced forward a distance "a", the injecting injection needle 312 is likewise advanced distally the same distance.

In operation, the endoscopic cannula 100 of the present disclosure may be used for a variety of clinical applications. In some embodiments, the endoscopic cannula 100 may be employed to inject substances into the heart. To that end, in some embodiments, the endoscopic cannula 100 of the present disclosure may be used to inject substances into tissue or organs of a patient. In some embodiments, the endoscopic cannula 100 of the present disclosure may be utilized for injecting cells into the heart to repair or regenerate regions of damaged or necrotic myocardium. Suitable cells that can be injected into the myocardium via the endoscopic cannula 100 of the present disclosure, include, but are not limited to, undifferentiated progenitor cells, undifferentiated satellite cells, undifferentiated stem cells, myocytes or other cells that can be used to repair a damaged myocardium. In some embodiments, the endoscopic cannula 100 of the present disclosure may be utilized for injecting one or more genes into the cells of myocardium for potential regenerative purposes. In some embodiments, the endoscopic cannula 100 of the present disclosure may be utilized for injecting into the cells of myocardium for potential regenerative purposes one or more proteins or peptides. For example, the endoscopic cannula 100 of the present disclosure may be used to inject transcription factors into cells of myocardium to induce the cells to exhibit characteristics of cardiomyocytes, such as described, for example, in Qian et al, "In Vivo Reprogramming of Murine Cardiac Fibroblasts Into Induced Cardiomyocytes," Nature, published online Apr. 18, 2012, which is incorporated herein by reference in its entirety.

Figure 5:
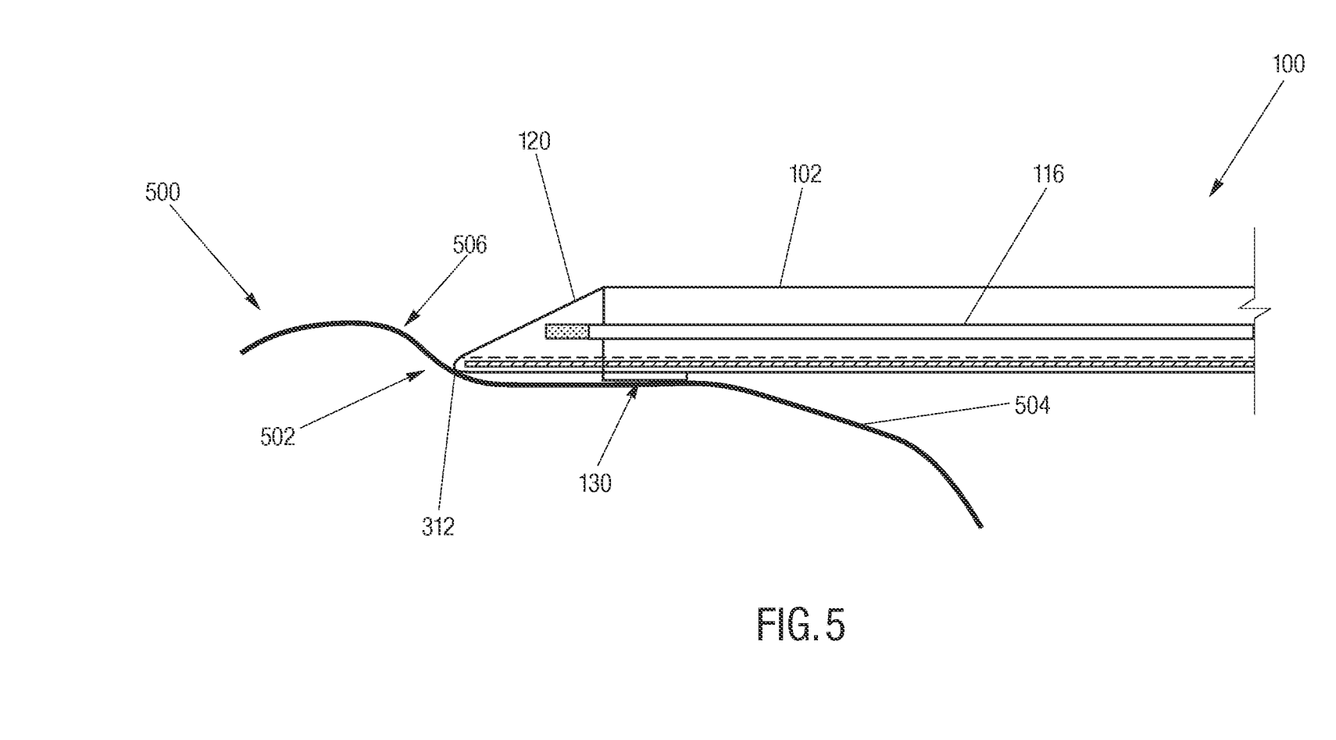
FIGS. 5-8 illustrate an embodiment method of using an endoscopic cannula of the present disclosure in operation to inject a substance into the heart of a patient.

In reference to FIG. 5, the endoscopic cannula 100 may be inserted into a body of the patient through a small percutaneous incision, and advanced to tissue at a site of issue, for example, the heart 500. Once at the heart 500, the visualization tip 120 of the endoscopic cannula 100 may be used to retract the pericardium away from the epicardial surface 504 to advance the distal end 106 of the endoscopic cannula 100 to a site of injection 502 into the myocardium of the heart 500. The endoscopic cannula 100 may be oriented on the epicardial surface 504 so that the suction pod 130 is positioned in contact with the epicardial surface 504 proximally to the injection site 502. In the embodiments where the endoscopic cannula 100 is provided with the flat bottom surface 108, the bottom surface 108 may assist the user in orienting the endoscopic cannula 100 on the epicardial surface 504. The suction pod 130 may then be activated to temporarily attach the endoscopic cannula 100 to the epicardial surface 504, thereby stabilizing the epicardial surface 504 in proximity to the injection site 502 and the endoscopic cannula 100 relative to the injection site 502. Next, downward pressure can be exerted on the epicardial surface 504 via the substantially rigid endoscopic cannula 100 to deform the epicardial surface 504 in vicinity of the injection site 502 in order to create a surface ledge 506 distal to the endoscopic cannula 100. The surface ledge 506 may be substantially perpendicular to the working channel 130 so as to permit a substantially perpendicular entry of the injection needle 312 into the myocardium of the heart 500.

Still in reference to FIG. 5, in operation, relative positions of the viewing channel 308, the working channel 310 and the suction channel 320 with respect to one another may provide stabilization of the epicardial surface, accurate alignment of the needle with the injection site, and improved visual control of the injection process. For example, positioning the working channel 310 between the viewing channel 308 and the epicardial surface to which the cannula 100 is attached and above the suction channel 320 may allow for unobstructed, continuous viewing of the needle advancement through the working channel 310 throughout the injection procedure. It may also confirm that the endoscope is positioned so as to allow the user to view the procedure from a desired direction, i.e. from above rather than from a side, or vise versa. By way of another non-limiting example, to prevent damage to surrounding tissue, the needle needs to be oriented to align the needle with the injection site. As noted above, in some embodiments, the endoscopic cannula 100 may be provided with a flat bottom surface 108 to assist in orientating the endoscopic cannula 100 in a desired position prior to injection.

Figure 6:
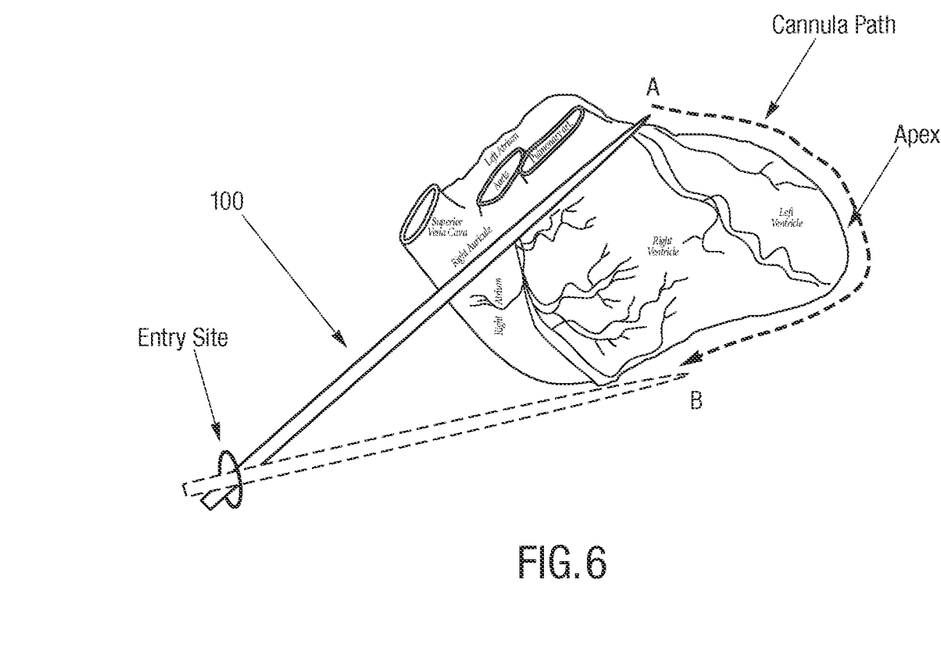
Figure 7:
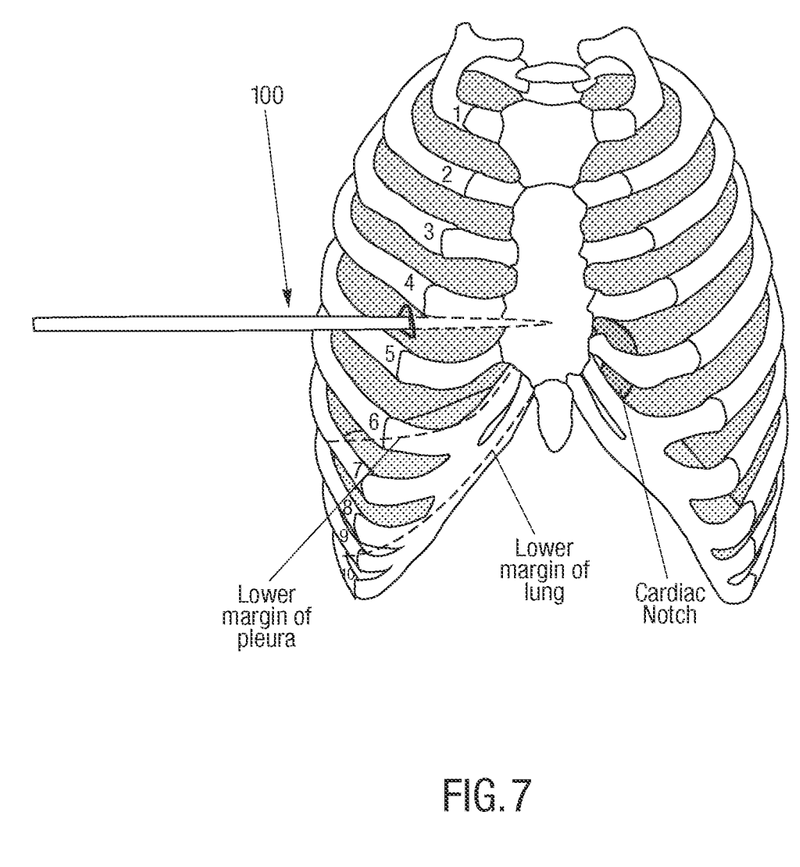
Figure 8:
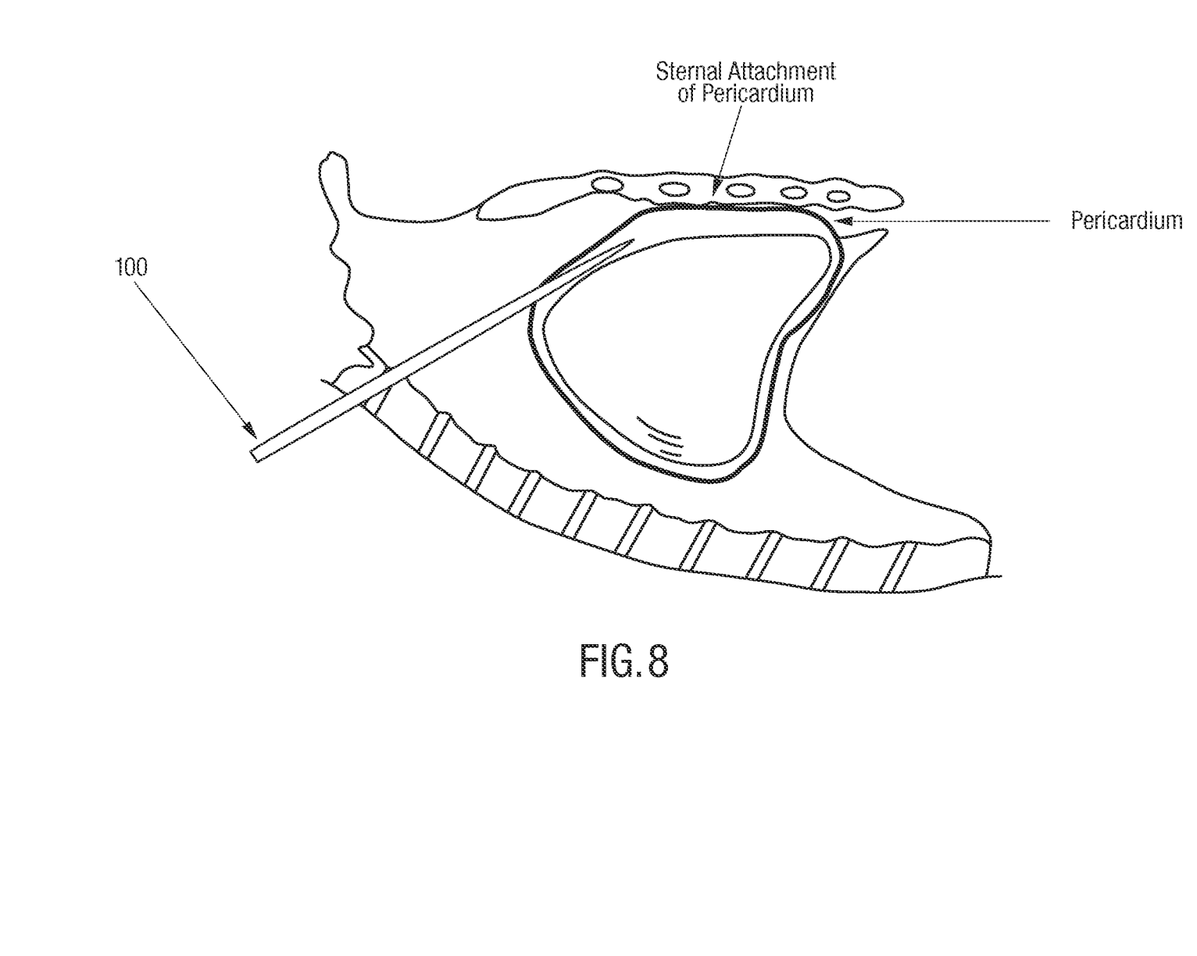

FIGS. 6-8 illustrate a non-limiting example of a method of using an endoscopic cannula of the present disclosure. The endoscopic cannula 100 may be entered through the pericardial sac surrounding the heart, and access both the anterior and posterior epicardial surfaces for visualization and therapy. In some embodiments, an intercostal incision can be made and a thoracoscopic port may be inserted into the incision. The endoscopic cannula 100 may be advanced through the port in the lateral intercostal space (either left or right sided), approximately in the $3^{rd}$, $4^{th}$ or $5^{th}$ intercostal space. Access may be achieved by performing a 2 cm skin incision and bluntly dissecting the intercostal muscles to enter the pleural cavity. A thoracoscopic port may be inserted into the incision.

In reference to FIG. 6, entry of the cannula via a lateral intercostal thoracoscopic site may allow access to both anterior and posterior epicardial surfaces. The cannula is placed anterior to the heart upon entry through the pericardium. It may then be moved inferiorly to the apex of the heart, and continued along the contour of the heart to the posterior epicardial surface. Both anterior and posterior aspects of the heart may be accessed via a single entry point.

In reference to FIG. 7, the endoscopic cannula 100 may then be advanced through the pleural cavity (the lung may collapse upon incision through the pleura), and the endoscopic cannula 100 may be used to enter through the apposed pleura and pericardial layers near their sternal attachment sites anterior to the surface of the heart.

In reference to FIG. 8, pericardial puncture may be performed anterior to the heart, near the pericardium's sternal attachment. The pericardium's sternal attachment may provide counter-traction to allow the cannula tip to puncture the pericardial sac. When the patient is in a supine position, the pericardium's sternal attachment may suspend the heart within the pericardial sac to provide space anterior to the epicardial surface for safe entry by the cannula. With the visualization tip 120 of the endoscopic cannula 100 placed at the site of entry, the injection needle 312 may be advanced several millimeters through the pleura and pericardium to make a puncture into the intra-pericardial space anterior to the surface of the heart. The injection needle 312 may then be retracted, and the visualization tip 120 may be advanced through the puncture into the intra-pericardial space anterior to the surface of the heart. With the patient in a supine position, gravity may suspend the heart within the pericardial sac, thereby providing space anterior to the surface of the heart for entry of the endoscopic cannula.

Referring back to FIG. 5, the endoscopic cannula 100 may then be advanced into the desired position on the surface of the heart, under direct visual guidance by the endoscope, and vacuum may be applied to the suction pod to stabilize the cannula on the surface of the beating heart. The wet surface of the heart may allow the position of the endoscopic cannula 100 to be adjusted even as suction is applied, while stabilizing the endoscopic cannula 100 on the beating heart. Such stabilization may be desired to maintain precise control during needle advancement and injection, despite epicardial movement during myocardial contraction, thus avoiding puncture of nearby coronary vessels. With suction applied, visual guidance and needle injection into the heart may be performed by a single operator.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, and as fall within the scope of the following claims.

What is claimed is:

1. An endoscopic cannula, comprising:
an elongated body having a proximal end and a distal end;
a visualization tip located at the distal end of the elongated body, the visualization tip being beveled, with a lower region in linear alignment with a bottom surface of the elongated body and a tapered upper region terminating in an apex with the lower region, the bottom surface of the elongated body defining a planar surface for orienting the elongated body on a tissue surface;
a sealed space in the visualization tip;
a viewing channel extending through the elongated body into the sealed space of the visualization tip, the viewing channel being configured for passing therethrough an endoscope in to the sealed space for viewing outside the visualization tip, the sealed space being disposed between the viewing channel and a wall forming the tapered upper region;
a working channel extending through the elongated body and through the apex of the visualization tip distally past the viewing channel, the working channel being configured for passing therethrough an injection needle distally of the elongated body;
a suction pod disposed on the bottom surface of the elongated body, the suction pod being in communication with a suction channel extending through the elongated body to create suction between the suction pod and a tissue surface to temporarily attach the elongated body to the tissue surface.

2. The endoscopic cannula of claim 1 wherein the working channel is positioned between the viewing channel and the bottom surface.

3. The endoscopic cannula of claim 1 wherein the suction pod is formed from a porous material.

4. The endoscopic cannula of claim 1 wherein the suction pod is positioned at the distal end of the elongated body.

5. The endoscopic cannula of claim 1 wherein the injection needle extends through the working channel and through a straight lower region of the visualization tip.

6. The endoscopic cannula of claim 1 wherein the tapered upper region of the visualization tip is fluidly connected to the viewing channel for passing the endoscope into the visualization tip and the working channel is extended through a straight lower region.

7. An endoscopic cannula, comprising:
an elongated body having a superior aspect and an inferior aspect;
a visualization tip located at a distal end of the elongated body, the visualization tip being beveled, with a lower region in linear alignment with a bottom surface of the elongated body, the bottom surface of the elongated body defining a planar surface for orienting the elongated body on a tissue surface and a tapered upper region terminating in an apex with the lower region;

a viewing channel extending through the elongated body into the visualization tip, the viewing channel being configured for passing therethrough an endoscope for viewing outside the visualization tip, wherein a sealed space is disposed between the viewing channel and a wall forming the tapered upper region;

a working channel extending through the elongated body and through the apex of the visualization tip distally past the viewing channel, the working channel being configured for passing therethrough an injection needle distally of the elongated body;

a suction pod disposed on the bottom surface of the inferior aspect of the elongated body, the suction pod being in communication with a suction channel extending through the elongated body to create suction between the suction pod and a tissue surface to temporarily attach the elongated body to the tissue surface.

8. The endoscopic cannula of claim 7 wherein the suction pod is formed from a porous material.

9. The endoscopic cannula of claim 7 wherein the suction pod is positioned at a distal end of the elongated body.

10. The endoscopic cannula of claim 7 wherein the tapered upper region of the visualization tip is fluidly connected to the viewing channel for passing the endoscope into the visualization tip and the working channel is extended through a straight lower region.

* * * * *